US00RE46479E

(19) United States
(12) Reissued Patent
Sansinena et al.

(10) Patent Number: US RE46,479 E
(45) Date of Reissued Patent: Jul. 18, 2017

(54) ELECTROCHEMICAL DETECTION OF SINGLE MOLECULES USING ABIOTIC NANOPORES HAVING ELECTRICALLY TUNABLE DIMENSIONS

(75) Inventors: Jose-Maria Sansinena, Los Alamos, NM (US); Antonio Redondo, Los Alamos, NM (US); Virginia Olazabal, Los Alamos, NM (US); Mark A. Hoffbauer, Los Alamos, NM (US); Elshan A. Akhadov, Los Alamos, NM (US)

(73) Assignee: LOS ALAMOS NATIONAL SECURITY, LLC, Los Alamos, NM (US)

(21) Appl. No.: 13/339,010

(22) Filed: Dec. 28, 2011

Related U.S. Patent Documents

Reissue of:
(64) Patent No.: 7,638,034
Issued: Dec. 29, 2009
Appl. No.: 11/525,329
Filed: Sep. 21, 2006

(51) Int. Cl.

| | |
|---|---|
| ***B81B 7/00*** | (2006.01) |
| ***G01N 27/26*** | (2006.01) |
| ***B82Y 15/00*** | (2011.01) |
| ***G01N 33/487*** | (2006.01) |

(52) U.S. Cl.
CPC ..... *B82Y 15/00* (2013.01); *G01N 33/48721* (2013.01)

(58) Field of Classification Search
USPC ..... 205/775, 789; 204/400, 403.01, 409
See application file for complete search history.

(56) References Cited

U.S. PATENT DOCUMENTS

| | | | | |
|---|---|---|---|---|
| 5,578,188 | A | 11/1996 | Mertens et al. | |
| 6,994,314 | B2 * | 2/2006 | Garnier et al. | B81B 3/0035 251/129.06 |
| 7,168,680 | B2 * | 1/2007 | Koeneman | F15C 5/00 251/129.06 |
| 7,238,485 | B2 | 7/2007 | Akeson | |
| 7,250,115 | B2 * | 7/2007 | Barth | B82Y 5/00 204/192.34 |
| 7,553,730 | B2 * | 6/2009 | Barth et al. | 438/270 |
| 7,638,024 | B2 | 12/2009 | Morita | |
| 7,638,034 | B2 | 12/2009 | Sansinena | |
| 7,923,237 | B2 | 4/2011 | Castro | |

(Continued)

FOREIGN PATENT DOCUMENTS

EP 1712891 A2 10/2006

OTHER PUBLICATIONS

Schmidt, "Stochastic Sensors," J. mater. Chem., 2005, 15; pp. 831-840.

(Continued)

*Primary Examiner* — Krisanne Jastrzab
(74) *Attorney, Agent, or Firm* — Pillsbury Winthrop Shaw Pittman LLP

(57) ABSTRACT

A barrier structure for use in an electrochemical stochastic membrane sensor for single molecule detection. The sensor is based upon inorganic nanopores having electrically tunable dimensions. The inorganic nanopores are formed from inorganic materials and an electrically conductive polymer. Methods of making the barrier structure and sensing single molecules using the barrier structure are also described.

61 Claims, 7 Drawing Sheets

(56) References Cited

U.S. PATENT DOCUMENTS

| | | | | |
|---|---|---|---|---|
| 8,968,545 | B2 | 3/2015 | Holt | |
| 2002/0140414 | A1* | 10/2002 | Sohn et al. | 324/71.4 |
| 2003/0032203 | A1 | 2/2003 | Sabatini | |
| 2005/0023156 | A1* | 2/2005 | Ramsey et al. | B01L 3/502707 205/792 |
| 2006/0231419 | A1 | 10/2006 | Barth | |
| 2006/0275927 | A1 | 12/2006 | Dubin et al. | |
| 2007/0114135 | A1 | 5/2007 | Kim et al. | |
| 2007/0298511 | A1 | 12/2007 | Kang | |
| 2008/0160635 | A1 | 7/2008 | Castro | |
| 2008/0312610 | A1 | 12/2008 | Binks | |
| 2009/0167288 | A1 | 7/2009 | Reid | |
| 2009/0283412 | A1 | 11/2009 | Sansinena | |
| 2010/0038243 | A1* | 2/2010 | White | G01N 27/333 204/416 |
| 2010/0075328 | A1 | 3/2010 | Bjornson | |
| 2010/0289505 | A1 | 11/2010 | Zhang | |
| 2010/0310421 | A1 | 12/2010 | Oliver | |
| 2010/0327255 | A1 | 12/2010 | Peng | |
| 2010/0331194 | A1 | 12/2010 | Turner | |
| 2011/0120890 | A1 | 5/2011 | Macpherson | |
| 2011/0136676 | A1 | 6/2011 | Greene | |
| 2011/0297542 | A1 | 12/2011 | Smyth | |
| 2012/0034410 | A1 | 2/2012 | Baumgart | |
| 2012/0097539 | A1 | 4/2012 | Qian | |
| 2013/0048499 | A1 | 2/2013 | Mayer | |

OTHER PUBLICATIONS

Svehla et al., 'Nano-Fabricated Size Exclusion Chromatograph,' Jet Propulsion Technical Report (2002).

Clarke et al., 'Continuous base identification for single-molecule nanopore DNA sequencing,' Nature Nanotechnology 4, 265-270 (2009).

Ayub et al., 'Precise electrochemical fabrication of sub-20 nm solid-state nanopores for single-molecule biosensing,' J. Phys.: Condens. Matter 22 (2010), IPO Publishing.

Sayre et al. (1997) Electrooxidative Deposition of Polypyrrole and Polyaniline on Self-Assembled Monolayer Modified Electrodes. Langmuir, 13:714-722.

Derrington et al. (2010) Nanopore DNA sequencing with MspA. PNAS, 107 (37):16060-16065.

Malinauskas et al., 'Topical Review, Conducting polymer-based nanostructured materials: electrochemical aspects,' Nanotechnology 10P, Bristol, GB, vol. 16, No. 10, Oct. 1, 2005, R51-R62.

Sansinena et al., 'Micro-patterning of ionic reservoirs within a double bilayer lipid membrane to fabricate a 2D array of ion-channel switch based electrochemical biosensors,' 2004 NSTI Nanotechnology Conference and Trade Show, vol. 1, Jan. 1, 2004, pp. 221-223.

Office Action issued on Sep. 6, 2015 in Chinese Application No. 201280073673.9.

Shao et al., (2005) Conducting polymer polypyrrole supported bilayer lipid membranes. Biosensor and Bioelectronics, 20:1373-1379.

Xu et al., (2005) Reversible Conversion of Conducting Polymer Films from Superhydrophobic to Superhyrophilic, Angewandte Chemie International Edition, 44:6009-6012.

Yue et al., Nanochannel and Its Application in Analytical Chemistry, 2009, Recent Advances in Biology, Biophysics, Bioengineering and Computational Chemistry, Editors: Cornelia A. Bulucea, Valerie Mladenov, Emil Pop, Monica Leba, Nikos Mastorakis, pp. 80-93.

Hiroshi, Awaji et al., Synthesis of heterosegment-junctioned hybrid nanotubes of polythiophene and heterometallic nanoparticlesby sequential template-based electropolymerization, Chem. Commun., 2011. 47, pp. 6547-3549.

U.S. Office Action dated Feb. 14, 2017 for U.S. Appl. No. 14/289,388; (24 pages).

U.S. Office Action dated Feb. 14, 2017 for U.S. Appl. No. 14/289,445; (26 pages).

Peteu et al, ASC Abstract of Papers, 227th ACS National Meeting, 2004.*

Cornell et al, Nature, 387, pp. 580-583, 1997.*

Bayley et al., "Stochastic Sensing with Protein Pores," Adv. Mater. 2000, 12, No. 2, pp. 139-142.

Bayley et al., "Resistive-Pulse Sensing-From Microbes to Molecules," Chem. Rev. 2000, 100, pp. 2575-2594.

Trojanowicz, "Miniaturized Biochemical Sensing Devices Based on Planar Bilayer Lipid Membranes," Fresenius J. Anal Chem (2001) 371, pp. 246-260.

Schmidt, "Stochastic Sensors," J. mater. Chem., 2005, 15, pp. 831-840.

Cheng et al., "Single Ion Channel Sensitivity in Suspended Bilayers on Micromachined Supports," Langmuir 2001, 17, 4, pp. 1240-1242.

Mara et al., "An Asymmetric polymer Nanopore for Single Molecule Detection," Nano Letters, 2004, vol. 4, No. 3, pp. 497-501.

Li et al., "Ion-Beam Sculpting at Nanometere Length Scales," Nature, vol. 412, pp. 166-169, 2001.

Saleh et al., "An Artificial Nanopore for molecular Sensing," Nano Letters, 2003, vol. 3, No. 1, pp. 37-38.

Bayley et al., "Stochastic Sensors Inspired by Biology," Nature, vol. 413, pp. 226-230, 2001.

* cited by examiner

ELECTROCHEMICAL DETECTION OF SINGLE MOLECULES USING ABIOTIC NANOPORES HAVING ELECTRICALLY TUNABLE DIMENSIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

STATEMENT REGARDING FEDERAL RIGHTS

This invention was made with government support under Contract No. DE-AC 52-06 NA 25396, awarded by the U.S. Department of Energy. The government has certain rights in the invention.

*CROSS-REFERENCE TO RELATED APPLICATIONS*

*More than one reissue application has been filed for U.S. Pat. No. 7,638,034. The instant application Ser. No. 13/339,010, filed Dec. 28, 2011 is a reissue application to U.S. Pat. No. 7,638,034 and two divisional reissue application Ser. Nos. 14/289,445, and 14/289,388, filed May 28, 2014, and further relates to International Patent Application No. PCT/US2012/031914, filed Apr. 2, 2012, U.S. patent application Ser. No. 13/437,793, filed Apr. 2, 2012, U.S. patent application Ser. No. 13/437,839, filed Apr. 2, 2012, U.S. patent application Ser. No. 13/437,817, filed Apr. 2, 2012, and U.S. patent application Ser. No. 13/437,753, filed Apr. 2, 2012, the entire disclosures of which are incorporated herein by reference in their entireties.*

*CROSS-REFERENCE TO RELATED APPLICATIONS*

*More than one reissue application has been filed for the reissue of U.S. Pat. No. 7,638,034. The reissue applications are U.S. patent application Ser. Nos. 14/289,445, 14/289,388 and 13/339,010 (the present application).*

*RELATED U.S. APPLICATION DATA*

*This application is a reissue application of U.S. Pat. No. 7,638,034, issued on Dec. 29, 2009.*

BACKGROUND OF INVENTION

The invention relates to barrier structures comprising nanopores. More particularly, the invention relates to structures having electroactive nanopores. Even more particularly, the invention relates to electrochemical sensors having such structures.

The detection and identification of single molecules has received increasing interest over the last few years, as there has been a realization that this can be done by analyzing transport and electrochemical phenomena through pores having nanoscale dimensions. Measurements of the ionic current through a single-protein channel incorporated into a freestanding lipid bilayer membrane can form the basis of a new and versatile method for single-molecule chemical and biological sensing, called stochastic sensing. These sensors consist of a protein pore embedded in an insulating membrane and operate by measuring the characteristic current through the pore in the presence of molecules of interest. The magnitude, duration, and rates of occurrence of the current blockage allow rapid discrimination between similar molecular species.

The main limitation in this nascent field is that the bulk of the work has been focused on biologically-based stochastic sensors using protein pores embedded in lipid bilayer membranes. The lipid bilayer membrane into which the channel is immobilized is fragile and unstable; such membranes have lifetimes on the order of a few hours and, very rarely, exceed one day. These membranes are extremely delicate and susceptible to breakage, requiring vibration isolation tables, low acoustic noise environments, and special solution handling. This is unacceptable for field-usable devices and applications outside the laboratory. Furthermore, although a range of membrane proteins, which can be modified as desired through biochemistry or mutagenesis, may be exploited as sensors, the availability of biological pores is still limited with respect to having complete freedom in pore size, structure, and composition. Attempts to fabricate solid-state nanopores that are able to mimic the ion transport properties of protein ion channels lack reproducible dimensional control at the nanometer scale.

Existing biologically-based stochastic membrane sensors are not sufficiently robust for widespread use outside a controlled laboratory setting. Therefore, what is needed is a stochastic membrane sensor that is sufficiently robust to withstand use in applications under normal conditions. What is also needed is a membrane for a stochastic sensor that is not biologically-based. What is further needed is a membrane for a stochastic sensor having a diameter that is reproducibly controllable.

SUMMARY OF INVENTION

The present invention meets these and other needs by providing a barrier structure for use in an electrochemical stochastic membrane sensor for single molecule detection. The sensor is based upon inorganic nanopores having electrically tunable dimensions. The inorganic nanopores are formed from inorganic materials and an electrically conductive polymer. Methods of making the barrier structure and sensing single molecules using the barrier structure are also described.

Accordingly, one aspect of the invention is to provide a barrier structure. The barrier structure comprises: a first chamber; a second chamber; a barrier separating the first chamber and the second chamber. The barrier comprises at least one electroactive nanopore structure joining the first chamber and the second chamber. The at least one electroactive nanopore structure comprises: a wall defining a electroactive nanopore connecting the first chamber and the second chamber and having an electrically tunable diameter; a first electrode pair disposed in the wall, wherein electrodes of the first electrode pair are disposed at opposite ends of the electroactive nanopore, and wherein a first voltage across the first electrode pair attracts a plurality of molecules to the electroactive nanopore and drives the plurality of molecules through the electroactive nanopore; a second electrode pair disposed in the wall between the first electrode pair; and a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter. The barrier structure also comprises at least one power supply electrically coupled to the first electrode pair and the second electrode pair, wherein the at least one power supply provides the first voltage across the first electrode pair and the second voltage across the second electrode pair.

A second aspect of the invention is to provide an electroactive nanopore structure. The electroactive nanopore structure comprises: a wall defining a electroactive nanopore having a first open end and a second open end and having a electrically tunable diameter; a first electrode pair disposed in the wall, wherein electrodes of the first electrode pair are disposed at opposite ends of the electroactive nanopore, and wherein a first voltage across the first electrode pair attracts a plurality molecules to the electroactive nanopore and drives the plurality of molecules through the electroactive nanopore; a second electrode pair disposed in the wall between the first electrode pair; and a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter.

A third aspect of the invention is to provide a stochastic sensor structure. The stochastic sensor structure comprising: a first chamber; a second chamber; a barrier separating the first chamber and the second chamber, wherein the barrier comprises at least one electroactive nanopore structure joining the first chamber and the second chamber, wherein the at least one electroactive nanopore structure comprises: a wall defining a electroactive nanopore connecting the first chamber and the second chamber and having a electrically tunable diameter; a first electrode pair disposed in the wall, wherein electrodes of the first electrode pair are disposed at opposite ends of the electroactive nanopore, and wherein a first voltage across the first electrode pair attracts a plurality molecules to the electroactive nanopore and drives the plurality of molecules through the electroactive nanopore; and a second electrode pair disposed in the wall between the first electrode pair; and a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter; at least one power supply electrically coupled to the first electrode pair and the second electrode pair, wherein the at least one power supply provides the first voltage across the first electrode pair and the second voltage across the second electrode pair; and a current measuring device for measuring a current flowing between the first electrode pair, wherein the current corresponds to a predetermined molecular species.

A fourth aspect of the invention is to provide a method of making an electroactive nanopore structure. The electroactive nanopore structure comprises: a wall defining a electroactive nanopore having a first open end and a second open end and having a electrically tunable diameter; a first electrode pair having electrodes disposed at opposite ends of the electroactive nanopore; a second electrode pair comprising a second anode and a second cathode disposed in the wall between the first electrode pair; and a conductive polymer disposed over an electrode of the second electrode pair. The method comprises the steps of: providing a template comprising a strip of photocurable polymer; depositing alternating layers of conductive material and insulating material over the template, wherein the alternating layers form the first electrode pair and the second electrode pair, and wherein electrodes of the first electrode pair and the second electrode pair are separated by at least one layer of insulating material; removing the template to form the electroactive nanopore; and depositing the conductive polymer on the electrode of the second electrode pair.

A fifth aspect of the invention is to provide a method of sensing the presence of an analyte molecule. The method comprises the steps of: providing a sensor structure, the sensor structure comprising a sampling chamber, a collection chamber, and a separation structure separating the sampling chamber and the collection chamber, wherein the separation structure includes a electroactive nanopore structure comprising: a wall defining a electroactive nanopore connecting the sampling chamber and the collection chamber and having a electrically tunable diameter; a first electrode pair having electrodes disposed at opposite ends of the electroactive nanopore; a second electrode pair disposed in the wall between the first electrode pair; and a conductive polymer disposed over an electrode of the second electrode pair; providing the analyte to the sampling chamber; passing the analyte molecule from the sampling chamber into the electroactive nanopore; applying a first voltage across the first electrode pair; and measuring a current across the first electrode pair, wherein the current is indicative of the presence of the analyte molecule.

A sixth aspect of the invention is to provide a method of controlling flow of a fluid between a first chamber and a second chamber. The method comprising the steps of: providing a barrier structure, wherein the barrier structure includes at least one electroactive nanopore structure, wherein the at least one electroactive nanopore structure comprises: a wall defining a electroactive nanopore connecting the first chamber and the second chamber and having a electrically tunable diameter; a first electrode pair disposed in the wall and having electrodes disposed at opposite ends of the electroactive nanopore; a second electrode pair disposed in the wall between the first electrode pair; and a conductive polymer disposed over an electrode of the second electrode pair; providing the fluid to the first chamber; passing the fluid from the first chamber into the electroactive nanopore; and increasing or decreasing the electrically tunable diameter of the electroactive nanopore to control the flow of the fluid through the electroactive nanopore to the second chamber.

These and other aspects, advantages, and salient features of the present invention will become apparent from the following detailed description, the accompanying drawings, and the appended claims.

DETAILED DESCRIPTION

Figure 1:
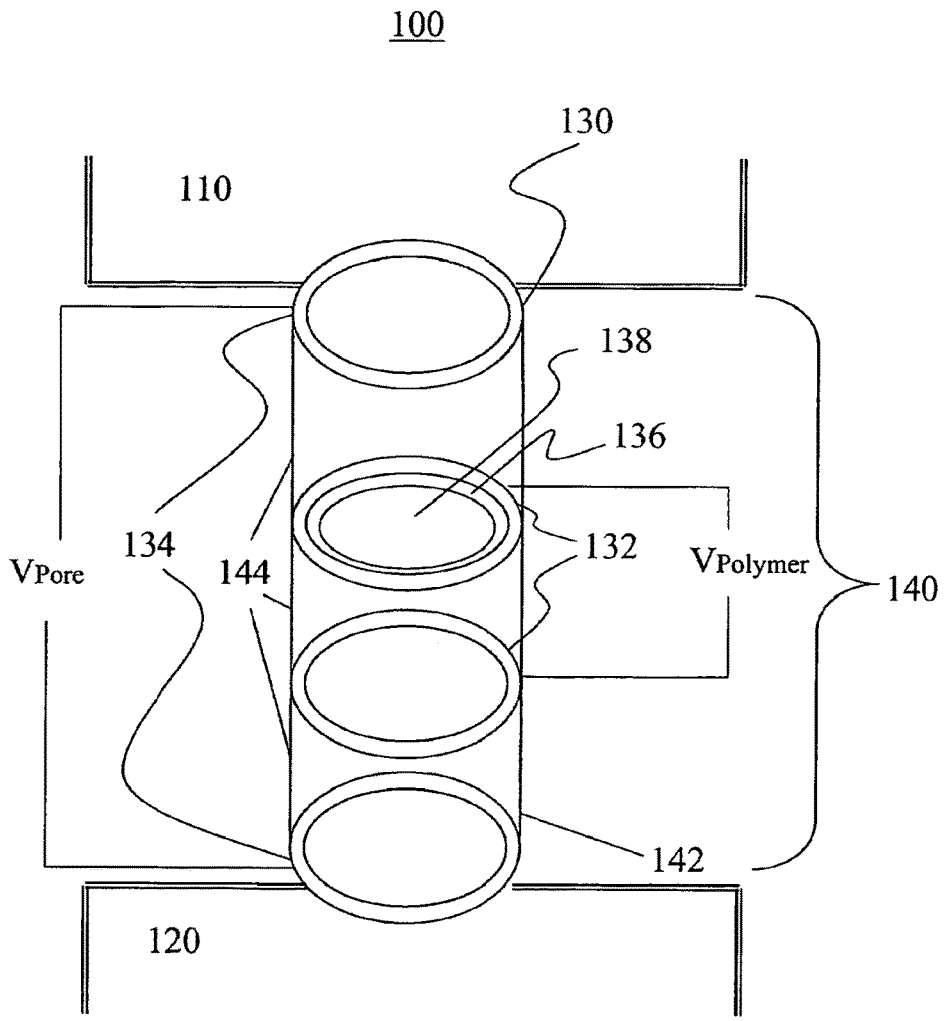
FIG. 1 is a schematic representation of a barrier structure.

In the following description, like reference characters designate like or corresponding parts throughout the several views shown in the figures. It is also understood that terms such as "top," "bottom," "outward," "inward," and the like are words of convenience and are not to be construed as limiting terms. In addition, whenever a group is described as either comprising or consisting of at least one of a group of elements and combinations thereof, it is understood that the group may comprise or consist of any number of those elements recited, either individually or in combination with each other.

Referring to the drawings in general and to FIG. 1 in particular, it will be understood that the illustrations are for the purpose of describing a particular embodiment of the invention and are not intended to limit the invention thereto. Turning to FIG. 1, a barrier structure of the present invention is shown. Barrier structure 100 comprises a first chamber 110, a second chamber 120 and a barrier 130 separating first chamber 110 and second chamber 120.

First chamber 110 and second chamber 120 are adapted to contain a fluid, and their dimensions and other characteristics depend on the specific application in which barrier structure is used. In one embodiment, for example, first chamber 110 may serve as a sampling chamber for collecting a fluid for analysis, and second chamber 120 may serve as an analysis chamber. Alternatively, first chamber 110 and second chamber 120 may simply be reservoirs for containing a fluid buffer, with barrier 140 limiting communication between the reservoirs.

Barrier 140 comprises at least one electroactive nanopore 130 having a wall defining a solid-state electroactive nanopore 130 and connecting first chamber 110 and second chamber 120. In one embodiment, barrier 140 comprises an array of electroactive nanopores 130. A first electrode pair 134, having two electrodes disposed at opposite ends of electroactive nanopore 130, is disposed in the nanopore wall at opposite ends of electroactive nanopore 130. The two electrodes of first electrode pair 134 are proximate to where wall 142 joins first chamber 110 and second chamber 120, respectively. A first voltage $V_{Pore}$, when applied across first electrode pair 134, attracts a plurality of molecules present in either first chamber or second chamber to electroactive nanopore 130 and drives the plurality of molecules through electroactive nanopore 130 and into the opposite chamber. First electrode pair 134 may comprise any conductive material known in the art such as, but not limited to, platinum, gold, graphite, electrically conductive metal alloys, combinations thereof, and the like.

A second electrode pair 132 comprising two electrodes is disposed in wall 142 between the electrodes of first electrode pair 134. Second electrode pair 132 may comprise any conductive material known in the art such as, but not limited to, platinum, gold, graphite, electrically conductive metal alloys, combinations thereof, and the like.

The electrodes of first electrode pair 134 and second electrode pair 132 are separated from each other by insulating material 144. Insulating material 144 comprises at least one of a metal oxide such as sapphire and silica ($SiO_2$), glasses, nonconductive polymers, silicon, and the like.

A conductive polymer 136 is disposed on the surface of wall 142 over an electrode of the second electrode pair 132. Conductive polymer 136 has electrically tunable dimensions; i.e., it is responsive to a second voltage $V_{Polymer}$, applied across second electrode pair 132, and is capable of expanding or contracting in response to the second voltage. The presence of conductive polymer 136 on the surface of the wall of electroactive nanopore 130 provides the electroactive nanopore 130 with an electrically tunable diameter 138 or cross-section. As conductive polymer 136 expands or contracts, its volume changes, causing the cross-section, or diameter 138, of electroactive nanopore 130 to correspondingly decrease and increase. Diameter 138 is also reversibly tunable—i.e., it may be decreased and then increased, or vice versa. Conductive polymer 136 comprises an ionically conductive polymer such as, but not limited to, polypyrrole, polyaniline, combinations thereof, and the like.

In the absence of a second voltage $V_{Polymer}$, electroactive nanopore 130 has a diameter 138 of up to about 50 nm. With the application of the second voltage $V_{Polymer}$, conductive polymer 136 may be expanded to decrease diameter 138 to a zero or near-zero value, effectively closing electroactive nanopore 130.

The thickness of each of the electrodes 132, 134 in electroactive nanopore 130 depends on the desired electrode size and the desired spacing between electrodes. The thicknesses of the individual layers of insulating material 140 must be sufficient to prevent shorting or arcing between the electrode layers. The individual electrodes and layers of insulating material 140 each have a thickness of up to 5 nm. In one embodiment, the thickness is in a range from about 1 nm to about 5 nm.

The length of electroactive nanopore 130 should be long enough to accommodate a single analyte molecule of interest. As analyte molecules of interest may vary from one application to another, the length of electroactive nanopore 130 may be varied accordingly. Electroactive nanopore 130 may, for example, have one length when used to detect the presence of proteins, another length when detecting polymers, and yet a third length when detecting DNA molecules. Electroactive nanopore 130 may have a length in a range from about 5 nm to about 50 nm. In one embodiment, electroactive nanopore 130 has a length of up to 5 nm, which approximates the length of protein pores that are used in stochastic sensors.

Figure 4A:
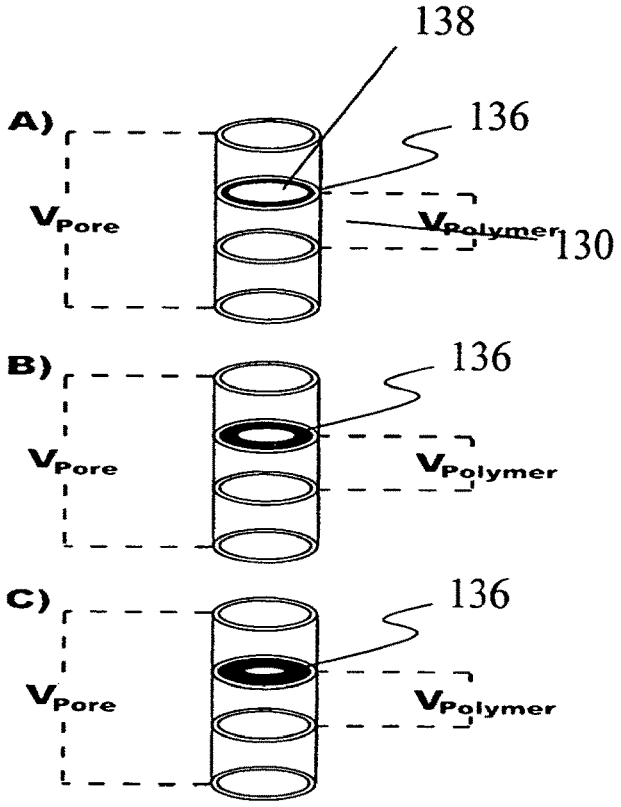
FIG. 4a is a schematic representation showing the response of the electrically tunable diameter of an electroactive nanopore to voltage $V_{Polymer}$.
Figure 4B:
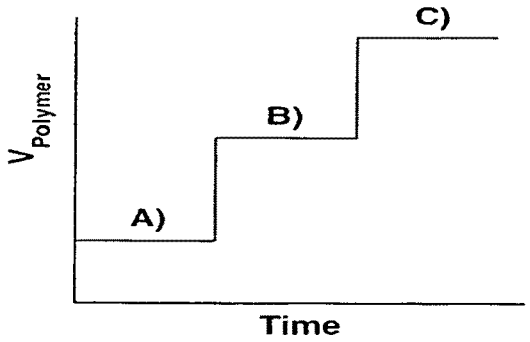
FIG. 4b is a plot of $V_{Polymer}$ as a function of time.
Figure 4C:
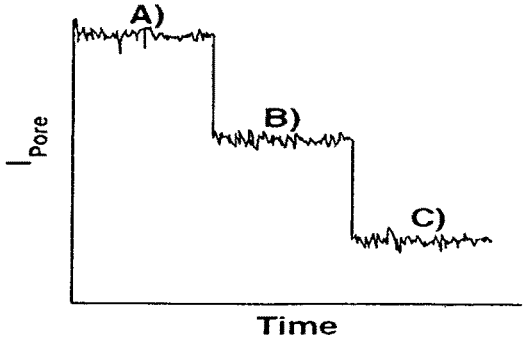
FIG. 4c is a plot of current $I_{Pore}$ passing through the electroactive nanopore, shown in FIG. 4a, as a function of time.

An example of how the current through electroactive nanopore 130 is affected by applying second voltage $V_{Polymer}$ across second electrode pair 132 and expanding conductive polymer 136 is illustrated in FIGS. 4a, 4b, and 4c. With first voltage $V_{Pore}$ across first electrode pair 134 held constant, $V_{Polymer}$ is increased from a low value (A in FIG. 4b) to a medium value (B) to a high value (C). Conductive polymer 136 correspondingly expands (FIG. 4a), narrowing the diameter of the electroactive nanopore. As diameter 138 decreases (and conductive polymer expands), the current through electroactive nanopore 130 decreases as well (FIG. 4c).

Figure 5:
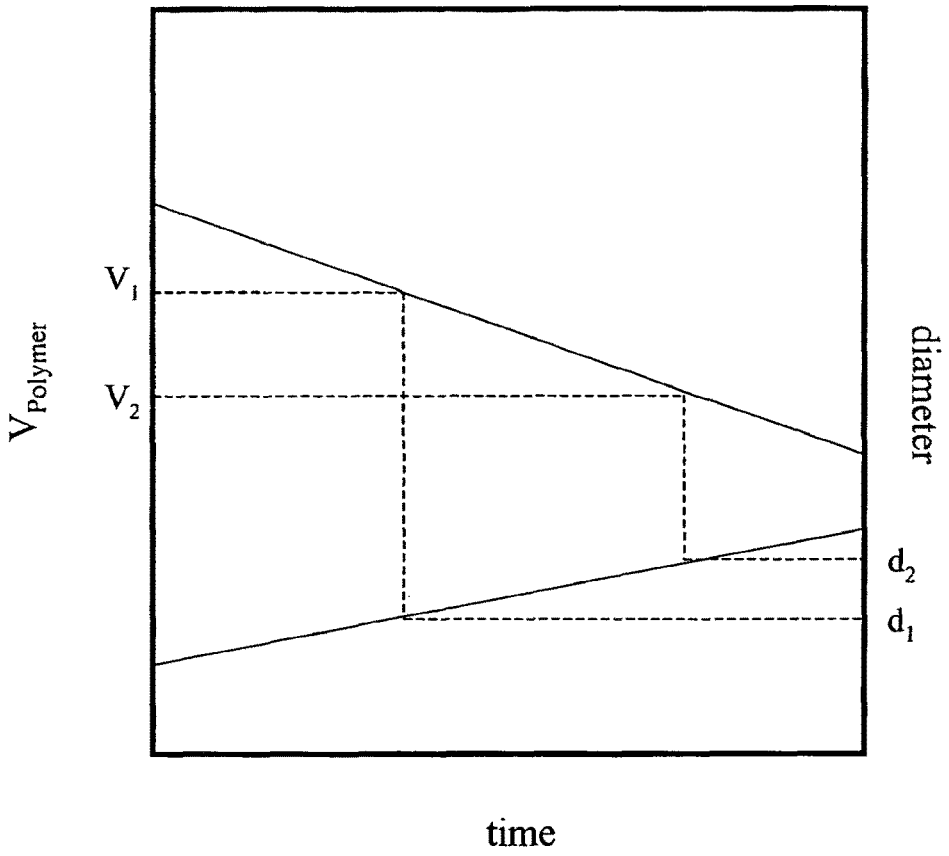
FIG. 5 is a plot of $V_{Polymer}$ and molecular diameter showing characteristic voltages $V_1$ and $V_2$ for molecules having diameters $d_1$ and $d_2$, respectively.

A characteristic voltage corresponding to the second voltage (while maintaining first voltage $V_{Pore}$ across first electrode pair 134 at a constant value) may be applied across second electrode pair 132 to tune diameter 138 to the approximate size. The application of characteristic voltages $V_1$ and $V_2$ for molecules having sizes of $d_1$ and $d_2$, respectively, is shown in FIG. 5. By applying voltage $V_1$ across second electrode pair 132, diameter 138 is tuned to the size of an analyte molecule having diameter $d_1$ while effectively preventing larger molecules having diameter $d_2$ from passing through electroactive nanopore 130.

At least one power source (not shown) is electrically coupled to first electrode pair 134 and second electrode pair 132, and provides the first voltage across first electrode pair 134 and second voltage across second electrode pair 132. The power source may be either a DC power source or an AC power source.

In one embodiment, barrier structure 100 forms a portion of a single-molecule—or stochastic—sensor that is adapted to detect particular species of analyte molecules present in a fluid. Such a sensor operates by measuring a characteristic current through electroactive nanopore 130 in the presence of analyte molecules of interest. The magnitude, duration, and rates of occurrence of the current blockage by the analyte molecule allow rapid discrimination between similar molecular species. Whereas previous stochastic sensors formed using protein pores embedded in lipid membranes are fragile and unstable, barrier structure 100 and electroactive nanopore 130 are structurally stable, due to their construction from inorganic materials and conductive polymers, and are capable of repeated use.

The selectivity of the stochastic sensor is based on the characteristic currents associated with the flow of different types of molecules in an ionic aqueous solution. The molecules have multiple measurable parameters that allow discrimination between different—but similar—species. For a selected diameter 138, each type of analyte molecule exhibits a different characteristic current and noise signature.

The stochastic sensor includes two buffer reservoirs, which are analogous to first chamber 110 and second chamber 120, joined by at least one electroactive nanopore 130. To detect the analyte molecule, first voltage $V_{Pore}$ is applied across first electrode pair 134, driving molecules through electroactive nanopore 130. The voltage applied between the second electrode pair 132 causes conductive polymer 136 to either expand or contract, thus controlling the diameter 138 of electroactive nanopore 130.

The selectivity of the stochastic sensor is based on the characteristic current signature associated with the flow of each type of analyte molecule through electroactive nanopore 130. Small ions flow through electroactive nanopore 130, producing a current having a relatively high value. When an analyte molecule having a diameter that is less than diameter 138 of electroactive nanopore 130 passes through the nanopore, the molecule partially occludes the passage of ions, thereby causing the current to decrease. After the analyte molecule traverses electroactive nanopore 130, normal ion flow through the nanopore resumes and the current is restored to its initial value. If an analyte molecule that is larger than diameter 138 of electroactive nanopore 130 tries to traverse the nanopore, the passage of ions through the nanopore is blocked and the current drops to zero. The polarity of first electrode pair 134 must then be reversed to unblock the nanopore. When the inner diameter 138 of electroactive nanopore 130 is increased by changing $V_{Polymer}$ to allow the analyte molecule to pass through the nanopore, the size of the molecule and its electrodynamic interactions with the charges in conductive polymer 136 will determine the current drop that is observed as the analyte molecule traverses electroactive nanopore 130.

Electroactive nanopore 130 can be electrochemically characterized by performing cyclic voltammetry between the electrodes of second electrode pair 132 in the presence of a buffer while maintaining a constant voltage across first electrode pair 134. The electrochemical behavior of electroactive nanopore 130 can then be characterized using the recorded cyclic voltammograms and the current across electroactive nanopore 130. Electroactive nanopore 130 is then closed by applying the appropriate voltage $V_{Polymer}$ across second electrode pair 132 while applying a constant independent voltage $V_{Pore}$ across first electrode pair 134 and monitoring the current through the nanopore. This yields a reference current for a state where substantially no molecules or ions—or a minimum number of molecules or ions—are passing through electroactive nanopore 130. Next, a sample containing a first analyte molecular species is introduced into either first chamber 110 or second chamber 120, and voltage $V_{Polymer}$ across second electrode pair 132 is decreased to slowly contract conductive polymer 136 and open electroactive nanopore 130. The resulting increase in diameter 138 of the nanopore results in a corresponding increase in ionic current through the nanopore. The characteristic voltage $V_{Polymer}$ associated with the first analyte molecular species is the voltage associated with the passage of the first analyte species through the nanopore.

Figure 6:
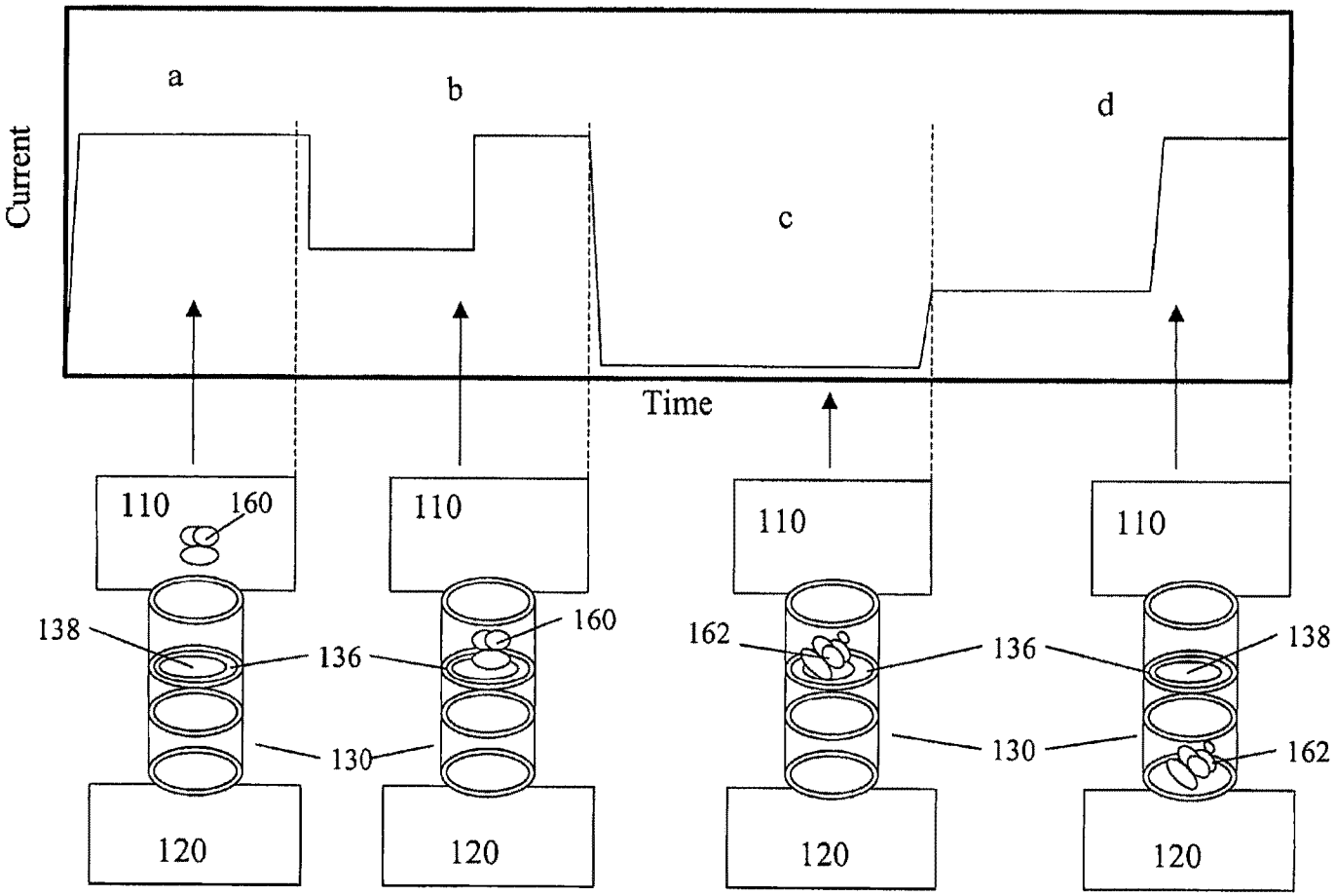
FIG. 6 is a schematic representation of the operation of a stochastic sensor.

FIG. 6 illustrates the principle of operation of the stochastic sensor. Initially, only small ions flow through electroactive nanopore 130, procuring a current having a relatively high value ((a) in FIG. 6). As one type of analyte molecule 160 that is smaller than diameter 138 passes through electroactive nanopore 130, the analyte molecule 160 partially occludes the passage of ions, causing the current to drop ((b) in FIG. 6). After the molecule has traversed electroactive nanopore 130, the current is restored to its original value, as shown in (b). In (c), a second type of analyte molecule 162, larger than diameter 138, tries to traverse electroactive nanopore 130. The passage of ions through electroactive nanopore 130 is completely blocked and the current goes to zero. Here, electroactive nanopore 130 may be unblocked by reversing the first voltage $V_{Pore}$. In (d), diameter 138 is increased by changing $V_{Polymer}$. The flow of ions—and the current—through electroactive nanopore 130 then resumes. The size of the second analyte molecule 162 and its electrodynamic interactions with the charges in conductive polymer 136 will determine the current drop when the molecule traverses electroactive nanopore 130. Once the second analyte molecule 162 exits electroactive nanopore 130, the current returns to its original value, as shown in (d).

The stochastic currents associated with molecules of the same species passing through electroactive nanopore 130 are monitored for later statistical analysis, which provides parameters, such as blockage currents, blockage times, blockage frequencies, current distribution, signal-to-noise ratios, and the like, that are used together with the characteristic voltage for identification of the analyte molecule.

If the analyte sample includes a mixture of molecules, random drops in current to either positive values or the reference current may occur, as some molecules pass through the electroactive nanopore 130 while others block the entrance to the nanopore. In such cases, the characterization process is typically repeated, and the voltage $V_{Polymer}$ across second electrode pair 132 is adjusted to the characteristic voltage of each analyte molecular species. In addition, the stochastic current is monitored for analytical purposes.

The stochastic sensor described hereinabove incorporates for the first time two important transport-selectivity capabilities into the field of sensor development. First, because diameter 138 of electroactive nanopore 130 can be modified in a controllable manner, the sensor can be used to cleanly separate different molecules on the basis of molecular size, ranging from simple ions to complex compounds and even microorganisms. Second, because the conductive polymer 136 can be charged in an ionic solution, the stochastic sensor can discriminate between molecules of similar size based on their different electrodynamic interactions with the conducting polymer.

Furthermore, the use of solid-state electroactive nanopores such as those described herein provides a significant advantage, as fabrication of an array of several pores can be integrated with electronics and on-chip computational hardware to provide a portable device capable of performing multiple sensing functions. Unlike sensors based on biological membranes and protein channels, this robust sensor will be stable and functional over a wider range of temperatures, solvents, voltages, and other potentially adverse conditions.

This new technology not only could be used in sensing but also in analytical chemistry, specifically in bio-separations, electroanalytical chemistry, and in the development of new approaches to DNA sequencing based on transport through the electroactive nanopore.

In another embodiment, barrier structure 100 forms a portion of a valve structure. Here, conductive polymer 136 may expand or contract in response to changes in voltage $V_{Polymer}$ across second electrode pair 132. As conductive polymer 136 expands or contracts, the tunable diameter 138 of electroactive nanopore 130 either decreases or increases, thereby regulating flow between first chamber 110 and second chamber 120.

In yet another embodiment, barrier structure 100 is a membrane that separates first chamber 110 and second chamber 120. Here, barrier structure 100 includes an array of electroactive nanopores 130. Based on the characteristic voltage signature associated with the flow of different types of molecules through electroactive nanopore 130, the membrane may be selectively tuned to allow certain molecular species to pass from first chamber 110 to second chamber 120.

Figure 2:
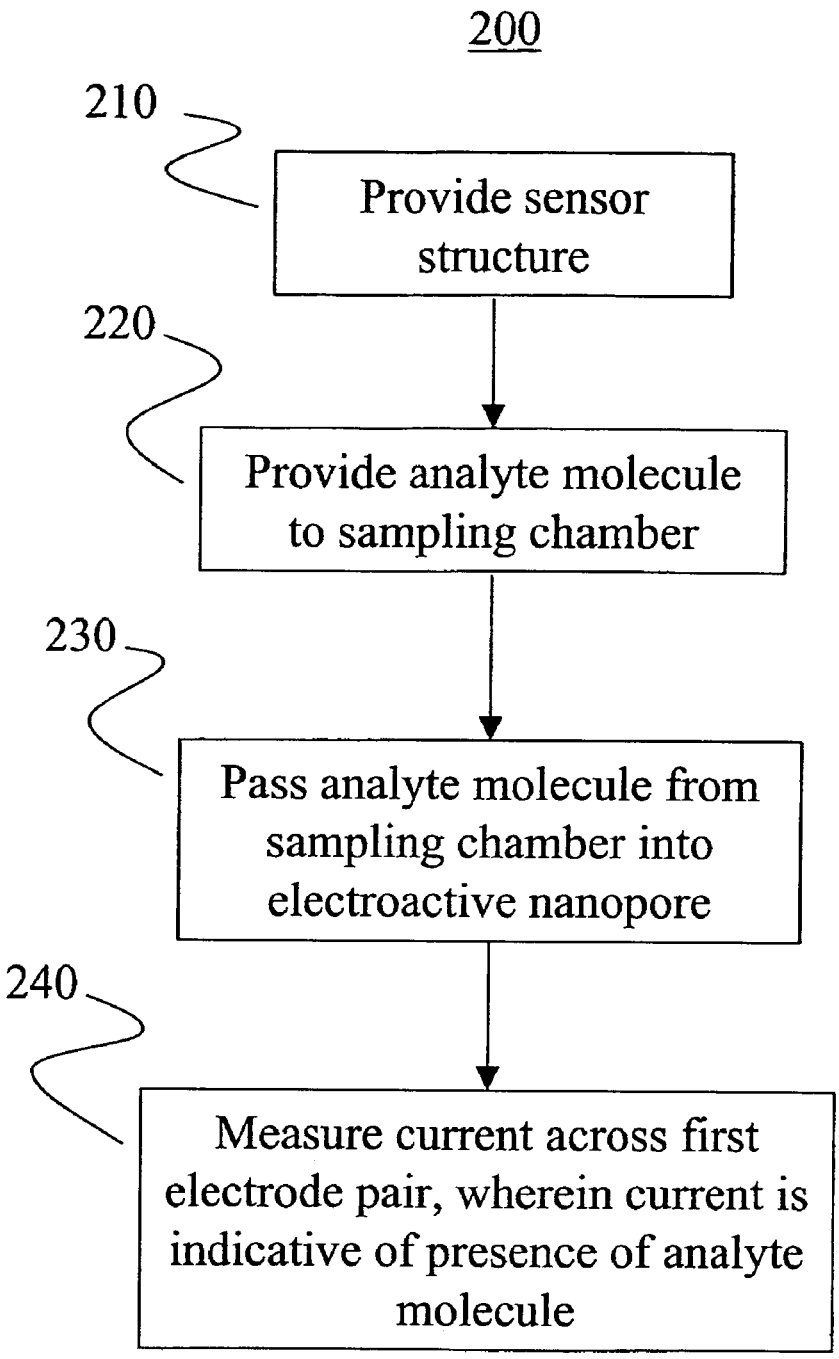
FIG. 2 is a flow chart for a method of sensing an analyte molecule.

The invention also includes a method of sensing an analyte molecule. A flow chart outlining the method is shown FIG. 2. In Step 210, a sensor structure comprising a sampling chamber, a collection chamber, and a separation structure is provided. The separation structure includes at least one electroactive nanopore 130, described herein and shown in FIG. 1. An analyte molecule in a buffer solution is provided to the sampling chamber (Step 220). The analyte molecule then passes from the sampling chamber into the electroactive nanopore in Step 230 by applying a first voltage $V_{Pore}$ across first electrode pair 134. As previously described herein, a current across first electrode pair 134 is generated by ions in the buffer solution passing through electroactive nanopore 130. When an analyte molecule having a diameter that is less than the diameter of electroactive nanopore 130 passes through the nanopore, the molecule partially occludes the passage of ions, thereby causing the current to decrease. After the analyte molecule traverses electroactive nanopore 130, normal ion flow through the nanopore resumes and the current is restored to its initial value. The size of the analyte molecule and its electrodynamic interactions with the charges in conductive polymer 136 will determine the current drop that is observed as the analyte molecule traverses electroactive nanopore 130. Accordingly, the current across the first electrode pair 132 is measured in Step 240 to determine whether the analyte molecule is present.

Figure 3:
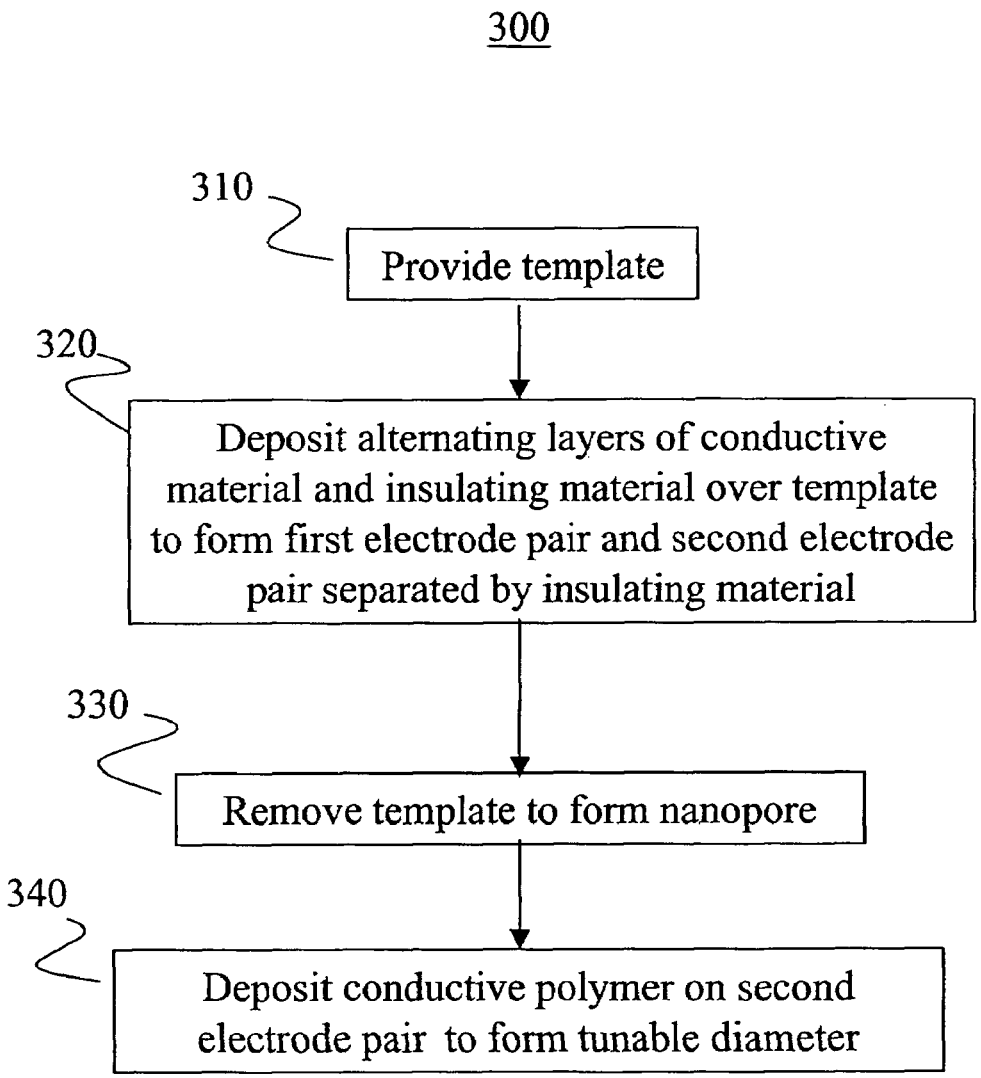
FIG. 3 is a flow chart for a method of making a barrier structure.

The invention also provides a method of making barrier structure 100 having electroactive nanopore 130. A flow chart of method 300 is shown in FIG. 3. In Step 310, a template is provided. The template comprises a strip of a photocurable polymer such as a polyimide or the like. The polymer strip, which is typically a few centimeters in length and less than 1 mm wide, is deposited on an insulating material such as sapphire, glass, or a silicon wafer. In one embodiment, the template includes a polymeric cylinder comprising the same photocurable polymer. The polymeric cylinder is vertically placed on top of the polymer strip. The polymeric cylinder has a diameter that is substantially equal to the desired maximum diameter of the electroactive nanopore. In one embodiment, the polymeric cylinder has a diameter of about 50 nm and a height of about 200 nm. In another embodiment, the polymeric cylinder is not provided.

In Step 320, alternating layers of conductive material and insulating material are deposited over the template to form a first—or outer—electrode pair and a second—or inner—electrode pair separated by at least one layer of insulating material. In one embodiment, the conductive material may comprise any conductive material known in the art such as, but not limited to, platinum, gold, graphite, conductive metal alloys known in the art, combinations thereof, and the like. The insulating material comprises at least one of a metal oxide, such as sapphire or silica ($SiO_2$), glasses, nonconductive polymers, silicon, or the like.

The thicknesses of the individual layers of insulating material must be sufficient to prevent shorting or arcing between the electrode layers. The thickness of the individual layers of conductive material depends on the desired electrode size and distance between electrodes. The individual layers of conductive and insulating material each have a thickness of up to 5 nm. In one embodiment, the thickness is in a range from about 1 nm to about 5 nm.

In one embodiment, the conductive layers and insulating layers are deposited using energetic neutral atom beam lithography/epitaxy (also referred to herein as "ENABLE"), which is described in U.S. Provisional Patent Application 60/738,624, filed on Nov. 21, 2005, by Mark A. Hoffbauer et al., entitled "Method of Forming Nanostructures on a Substrate," the contents of which are incorporated herein in their entirety.

The template is then removed (Step 330), typically by dissolution of the photocurable polymer. Where a polymer cylinder is provided, dissolution of the template leaves a microfluidic channel—or chamber—having a nanopore on top. In embodiments in which the template does not include the polymeric cylinder described above, the nanopore may be formed by drilling through the deposited conductive and insulating layers using a focused ion beam. The nanopore diameter reflects the size of the polymeric cylinder used in the template, and is typically about 50 nm. A second microfluidic channel or chamber is then formed from a polymeric material such as polydimethyl siloxane or the like. The second microfluidic chamber is then placed on top of the first microfluidic chamber such that the electroactive nanopore is enclosed between—and connects—the two chambers.

In Step 340, a conductive polymer film is electrochemically deposited on one electrode of the second electrode pair. The thickness of the conductive polymer film that is actually deposited depends on the diameter of the nanopore, in one embodiment, the thickness of the conductive polymer film is in a range from about 10 nm to about 50 nm. The conductive polymer comprises an ionic conductive polymer such as, but not limited to, polypyrrole, polyaniline, combinations thereof, and the like.

Method 300 can be optimized and updated for later fabrication of an array of several electroactive nanopores.

The nanopores can be integrated with electronics and on-chip computational hardware to do multiple sensing in a portable device.

Figure 7:
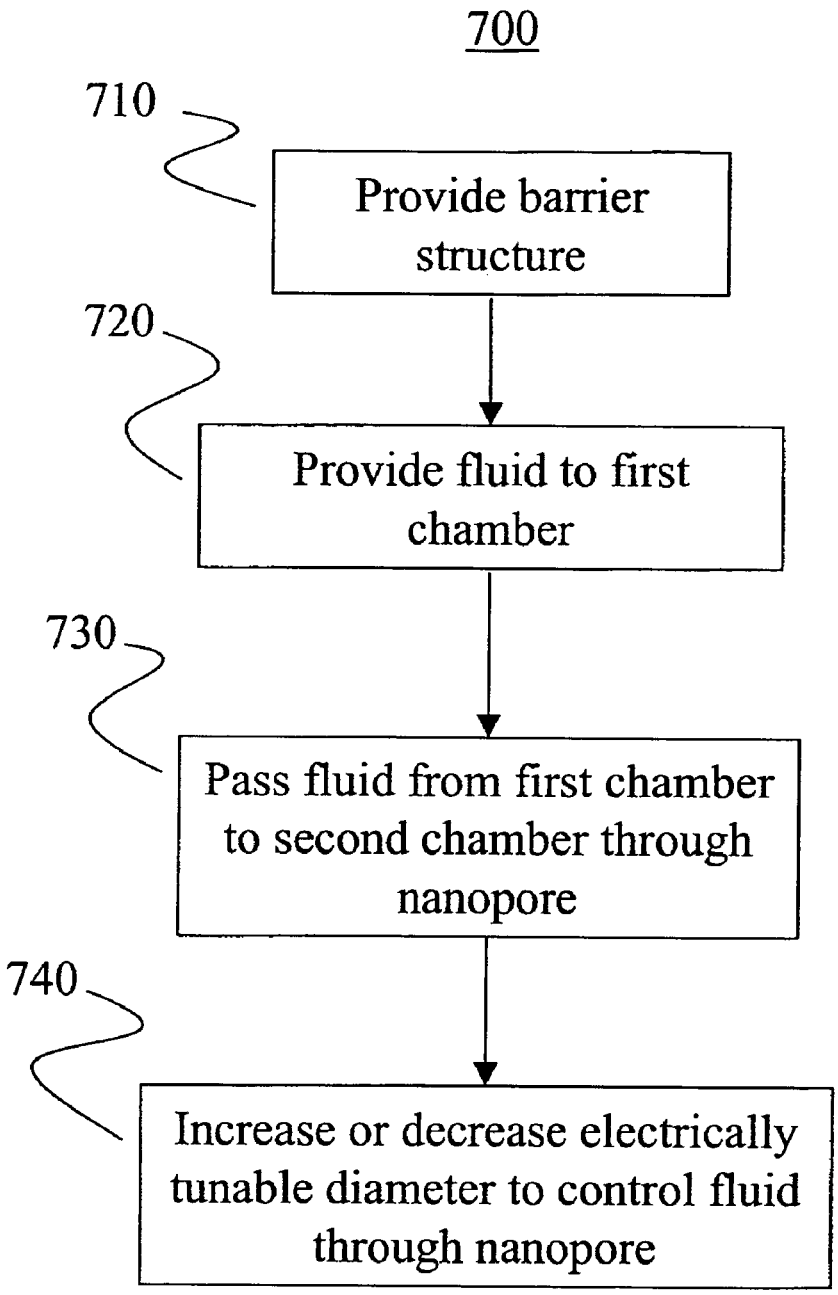
FIG. 7 is a flow chart for a method of controlling fluid.

The invention also provides a method of controlling fluid from a first chamber to a second chamber. A flow chart for method 700 is shown in FIG. 7. in step 710, a barrier structure, such as barrier structure 100 including at least one electro active nanopore 130 described hereinabove, is provided. Fluid is provided to the first chamber (Step 720) and is passed into the electroactive nanopore (Step 730). Step 730 is accomplished by applying a first voltage across first electrode pair 134 in electroactive nanopore 130. The first voltage is sufficient to cause the fluid to migrate from the first chamber through electroactive nanopore 130 to the second chamber. In Step 740, the electrically tunable diameter 138 of electroactive nanopore is either increased or decreased to control the flow of the fluid through electroactive nanopore 130 to the second chamber. The electrically tunable diameter may be either decreased or increased by applying a second voltage across second electrode pair 132 of electrode active nanopore 130. The second electrode voltage causes conductive polymer 136 to either expand or contract, which correspondingly causes electrically tunable diameter 138 to either decrease or increase.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

The invention claimed is:

1. A barrier structure, the barrier structure comprising:

a. a first chamber;

b. a second chamber;

c. a barrier separating the first chamber and the second chamber, wherein the barrier comprises at least one electroactive nanopore structure joining the first chamber and the second chamber, wherein the at least one electroactive nanopore structure comprises:

i. a wall defining a electroactive nanopore connecting the first chamber and the second chamber and having an electrically tunable diameter;

ii. a first electrode pair disposed in the wall, wherein electrodes of the first electrode pair are disposed at opposite ends of the electroactive nanopore, and wherein a first voltage across the first electrode pair attracts a plurality molecules to the electroactive nanopore and drives the plurality of molecules through the electroactive nanopore; and iii. a second electrode pair disposed in the wall between the first electrode pair; and iv. a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter; and d. at least one power supply electrically coupled to the first electrode pair and the second electrode pair, wherein the at least one power supply provides the first voltage across the first electrode pair and the second voltage across the second electrode pair.

2. The barrier structure according to claim 1, further including a current measuring device for measuring a current flowing between the first electrode pair, wherein the current corresponds to a predetermined molecular species.

3. The barrier structure according to claim 2, wherein the barrier structure forms a portion of a sensor.

4. The barrier structure according to claim 1, wherein each of the electrodes of the first electrode pair and the second electrode pair comprises one of platinum, gold, graphite, a metal alloy, and combinations thereof.

5. The barrier structure according to claim 1, wherein the first electrode pair and the second electrode pair are separated by an insulating material.

6. The barrier structure according to claim 1, wherein the insulating material comprises at least one of a glass, a metal oxide, a non-conductive polymer, and combinations thereof.

7. The barrier structure according to claim 1, wherein the conductive polymer is one of polypyrrole, polyaniline, and combinations thereof.

8. The barrier structure according to claim 1, wherein the barrier structure forms a portion of one of a valve structure and a membrane structure.

9. The barrier structure according to claim 1, wherein the at least one power supply includes a DC power supply.

10. An electroactive nanopore structure, the electroactive nanopore structure comprising:

a. a wall defining a electroactive nanopore having a first open end and a second open end and having a electrically tunable diameter;

b. a first electrode pair disposed in the wall, wherein electrodes of the first electrode pair are disposed at opposite ends of the electroactive nanopore, and wherein a first voltage across the first electrode pair attracts a plurality molecules to the electroactive nanopore and drives the plurality of molecules through the electroactive nanopore; and c. a second electrode pair disposed in the wall between the first electrode pair; and d. a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter.

11. The electroactive nanopore according to claim 10, wherein each of the electrodes of the first electrode pair and the second electrode pair comprises one of platinum, gold, graphite, a metal alloy, and combinations thereof.

12. The electroactive nanopore structure according to claim 10, wherein the first electrode pair and the second electrode pair are separated by an insulating material.

13. The electroactive nanopore structure according to claim 10, wherein the insulating material comprises a glass, a metal oxide, a non-conductive polymer, and combinations thereof.

14. The electroactive nanopore structure according to claim 10, wherein the conductive polymer is one of polypyrrole, polyaniline, and combinations thereof.

15. The electroactive nanopore structure according to claim 10, wherein the electroactive nanopore structure forms a portion of one of a valve structure, a sensor, and a membrane structure.

16. A stochastic sensor structure, the stochastic sensor structure comprising:

a. a first chamber;

b. a second chamber;

c. a barrier separating the first chamber and the second chamber, wherein the barrier comprises at least one electroactive nanopore structure joining the first chamber and the second chamber, wherein the at least one electroactive nanopore structure comprises:

i. a wall defining a electroactive nanopore connecting the first chamber and the second chamber and having a electrically tunable diameter;

ii. a first electrode pair disposed in the wall, wherein electrodes of the first electrode pair are disposed at opposite ends of the electroactive nanopore, and wherein a first voltage across the first electrode pair attracts a plurality molecules to the electroactive nanopore and drives the plurality of molecules through the electroactive nanopore; and iii. a second electrode pair disposed in the wall between the first electrode pair; and iv. a conductive polymer disposed over an electrode of the second electrode pair, wherein the conductive polymer is responsive to a second voltage across the second electrode pair and is capable of expansion or contraction in response to the second voltage, and wherein the expansion decreases the electrically tunable diameter and the contraction increases the electrically tunable diameter;

d. at least one power supply electrically coupled to the first electrode pair and the second electrode pair, wherein the at least one power supply provides the first voltage across the first electrode pair and the second voltage across the second electrode pair; and e. a current measuring device for measuring a current flowing between the first electrode pair, wherein the current corresponds to a predetermined molecular species.

17. A method of making a electroactive nanopore structure, wherein the electroactive nanopore structure comprises: a wall defining a electroactive nanopore having a first open end and a second open end and having a electrically tunable diameter; a first electrode pair having electrodes disposed at opposite ends of the electroactive nanopore; a second electrode pair comprising a second anode and a second cathode disposed in the wall between the first electrode pair; and a conductive polymer disposed over an electrode of the second electrode pair; the method comprising [the steps of]:

a. providing a template comprising a strip of photocurable polymer;

b. depositing alternating layers of conductive material and insulating material over the template, wherein the alternating layers form the first electrode pair and the second electrode pair, and wherein electrodes of the first electrode pair and the second electrode pair are separated by at least one layer of insulating material;

c. removing the template to form the electroactive nanopore; and d. depositing the conductive polymer on the electrode of the second electrode pair to form the electrically tunable diameter.

18. The method according to claim 17, wherein [the step of] depositing alternating layers of conductive material and insulating material over the template comprises:

a. depositing a first conductive layer over the template;

b. depositing a first insulating layer over the first conductive layer;

c. depositing a second conductive layer over the first insulating layer;

d. depositing a second insulating layer over the second conductive layer;

e. depositing a third conductive layer over the second conductive layer, wherein the second conductive layer and the third conductive layer form the second electrode pair;

f. depositing a third insulating layer over the third conductive layer; and g. depositing a fourth conductive layer over the third conductive layer, wherein the first conductive layer and the fourth conductive layer form the first electrode pair.

19. The method according to claim 17, wherein at least one of the first conductive layer, the first insulating layer, the second conductive layer, the second insulating layer, the third conductive layer, the third insulating layer, and the fourth conductive layer is deposited by energetic neutral beam lithography/epitaxy.

20. The method according to claim 17, wherein [the step of] depositing the conductive polymer comprises electrochemically depositing the conductive polymer onto at least one of the second anode and the second cathode.

21. The method according to claim 17, wherein the template further comprises a cylinder having a diameter that is substantially equal to the electrically tunable diameter of the electroactive nanopore, wherein the cylinder comprises the photcurable polymer.

22. The method according to claim 17, wherein [the step of] removing the template to form the electroactive nanopore comprises drilling through the alternating layers of conductive material and insulating material with a focused ion beam to form the electroactive nanopore.

23. A method of sensing the presence of an analyte molecule, the method comprising [the steps of]:

a. providing a sensor structure, the sensor structure comprising a sampling chamber, a collection chamber, and a separation structure separating the sampling chamber and the collection chamber, wherein the separation structure includes a electroactive nanopore structure comprising: a wall defining a electroactive nanopore connecting the sampling chamber and the collection chamber and having a electrically tunable diameter; a first electrode pair having electrodes disposed at opposite ends of the electroactive nanopore; a second electrode pair disposed in the wall between the first electrode pair; and a conductive polymer disposed over an electrode of the second electrode pair;

b. providing the analyte molecule to the sampling chamber;

c. passing the analyte molecule from the sampling chamber into the electroactive nanopore; and d. measuring a current across the first electrode pair, wherein the current is indicative of the presence of the analyte molecule.

24. The method according to claim 23, wherein [the step of] passing the analyte from the sampling chamber into the electroactive nanopore comprises applying a first voltage across the first electrode pair, wherein the first voltage is sufficient to cause the analyte to migrate from the sampling chamber through the electroactive nanopore structure to the collection chamber.

25. The method according to claim 23, further including the step of increasing or decreasing the electrically tunable diameter of the electroactive nanopore.

26. The method according to claim 23, wherein [the step of] increasing or decreasing the electrically tunable diameter of the electroactive nanopore comprises applying a second voltage across the second electrode pair, wherein the second electrode voltage causes the conductive polymer to either expand or contract.

27. A method of controlling flow of a fluid between a first chamber and a second chamber, the method comprising:

a. providing a barrier structure, wherein the barrier structure includes at least one electroactive nanopore structure, wherein the at least one electroactive nanopore structure comprises: a wall defining a electroactive nanopore connecting the first chamber and the second chamber and having a electrically tunable diameter; a first electrode pair disposed in the wall and having electrodes disposed at opposite ends of the electroactive nanopore; a second electrode pair disposed in the wall between the first electrode pair; and a conductive polymer disposed over an electrode of the second electrode pair;

b. providing the fluid to the first chamber;

c. passing the fluid from the first chamber into the electroactive nanopore; and d. increasing or decreasing the electrically tunable diameter of the electroactive nanopore to control the flow of the fluid through the electroactive nanopore to the second chamber.

28. The method according to claim 27, wherein passing the fluid from the first chamber into the electroactive nanopore comprises applying a first voltage across the first electrode pair, wherein the first voltage is sufficient to cause the fluid to migrate from the first chamber through the electroactive nanopore structure to the second chamber.

29. The method according to claim 27, wherein [the step of] increasing or decreasing the electrically tunable diameter of the electroactive nanopore comprises applying a second voltage across the second electrode pair, wherein the second electrode voltage causes the conductive polymer to either expand or contract, and wherein expansion of the conductive polymer increases the electrically tunable diameter and contraction of the conductive polymer decreases the electrically tunable diameter.

*30. A nanopore structure comprising a nanopore having an opening and a wall defining the nanopore, wherein the opening has an electrically tunable diameter.*

*31. A barrier structure comprising: a first chamber; a second chamber; a barrier separating the first chamber and the second chamber, wherein the barrier comprises at least one nanopore structure of claim 30 joining the first chamber and the second chamber.*

*32. The nanopore structure of claim 30, further comprising a first electrode pair, a second electrode pair between the first electrode pair, a conductive polymer disposed over an electrode of the second electrode pair, wherein the opening is an opening through the polymer.*

*33. The nanopore structure of claim 32, wherein the polymer is a conductive polymer.*

*34. A nanopore structure comprising a nanopore having an opening and a wall defining the nanopore, and one or more polymers on the wall, wherein the opening is electrically tunable.*

*35. A barrier structure comprising: a first chamber; a second chamber; a barrier separating the first chamber and the second chamber, wherein the barrier comprises at least one nanopore structure of claim 34 joining the first chamber and the second chamber.*

*36. The nanopore structure of claim 34, wherein the one or more polymers comprise a conductive polymer.*

*37. The nanopore structure of claim 34, further comprising a first electrode.*

*38. The nanopore structure of claim 37; wherein at least part of the one or more polymers is disposed over the first electrode.*

*39. The nanopore structure of claim 37, further comprising a second electrode and a third electrode, the first electrode being between the second electrode and the third electrode.*

*40. A method of controlling flow of a fluid through the nanopore structure of claim 30, the method comprising: passing the fluid through the opening; and tuning the electrically tunable diameter of the opening, so as to control flow of the fluid through the nanopore.*

*41. A method of controlling flow of an ionic species through the nanopore structure of claim 30, the method comprising: attracting the ionic species by a voltage through the opening; and tuning the electrically tunable diameter of the opening, so as to control flow of the ionic species through the nanopore.*

*42. A method of making a nanopore structure comprising a nanopore having an opening, and a wall defining the nanopore, the method comprising electrochemically depositing one or more materials on the wall, and forming the nanopore structure, wherein the opening is electrically tunable.*

*43. The method of claim 42, wherein the one or more materials comprise one or more polymers.*

*44. The method of claim 42, wherein the one or more materials comprise one or more electrical conductors.*

*45. A method of using the nanopore structure of claim 30, the method comprising passing an analyte molecule into the nanopore; and measuring a current through the nanopore.*

*46. A method of using the nanopore structure of claim 34, the method comprising passing an analyte molecule into the nanopore; and measuring a current through the nanopore.*

*47. A method of making a nanopore structure, the method comprising depositing a conductive layer over a template, the template comprising a cylinder; depositing an insulating layer over the conductive layer; removing the template to leave a nanopore through the conductive layer and the insulating layer; and depositing a conductive polymer, wherein the template comprise a strip of photocurable polymer.*

*48. The method of claim 47, wherein the cylinder comprises a photocurable polymer.*

*49. The method of claim 47, wherein the insulating layer comprises at least one of a metal oxide, glasses, nonconductive polymers, and silicon.*

*50. The method of claim 47, wherein the conductive layer comprises platinum, gold, graphite, conductive metal alloys, or a combination thereof.*

*51. A method of making a nanopore structure, the method comprising depositing a conductive layer over a template; depositing an insulating layer over the conductive layer; removing the template; forming a nanopore through the conductive layer and the insulating layer by a focused ion beam to expose the conductive layer in the nanopore; and depositing a conductive polymer, wherein the template comprise a strip of photocurable polymer.*

*52. The method of claim 51, wherein the insulating layer comprises at least one of a metal oxide, glasses, nonconductive polymers, and silicon.*

*53. The method of claim 51, wherein the conductive layer comprises platinum, gold, graphite, conductive metal alloys, or a combination thereof.*

*54. A device comprising the nanopore structure of claim 30.*

*55. A device comprising the nanopore structure of claim 31.*

*56. A device comprising the barrier structure of claim 34.*

*57. A device comprising the barrier structure of claim 35.*

*58. A sensor comprising the nanopore structure of claim 30.*

*59. A sensor comprising the nanopore structure of claim 31.*

*60. A sensor comprising the barrier structure of claim 34.*

*61. A sensor comprising the barrier structure of claim 35.*

* * * * *